United States Patent
Hodor et al.

(10) Patent No.: US 10,535,243 B2
(45) Date of Patent: Jan. 14, 2020

(54) TARGET BEHAVIOR MONITORING SYSTEM

(71) Applicant: HBH DEVELOPMENT, LLC, Woburn, MA (US)

(72) Inventors: Nathan Hodor, North Andover, MA (US); Brandon Herscovitch, Andover, MA (US); Barry Briggs, Arlington, MA (US)

(73) Assignee: HBH Development LLC, Woburn, MA (US)

( * ) Notice: Subject to any disclaimer, the term of this patent is extended or adjusted under 35 U.S.C. 154(b) by 11 days.

(21) Appl. No.: 15/795,533

(22) Filed: Oct. 27, 2017

(65) Prior Publication Data

US 2018/0122210 A1     May 3, 2018

Related U.S. Application Data

(60) Provisional application No. 62/414,163, filed on Oct. 28, 2016.

(51) Int. Cl.

| | |
|---|---|
| *G08B 21/04* | (2006.01) |
| *G08B 21/18* | (2006.01) |
| *A61B 5/103* | (2006.01) |
| *A61B 5/16* | (2006.01) |
| *A61B 5/00* | (2006.01) |

(Continued)

(52) U.S. Cl.
CPC .......... *G08B 21/0423* (2013.01); *A61B 5/103* (2013.01); *A61B 5/16* (2013.01); *A61B 5/6801* (2013.01); *G08B 21/0446* (2013.01); *G08B 21/182* (2013.01); *A61B 2562/0219* (2013.01); *G08B 3/10* (2013.01); *G08B 5/36* (2013.01); *G08B 6/00* (2013.01)

(58) Field of Classification Search
CPC ............ G08B 21/0423; G08B 21/0446; G08B 21/182; G08B 3/10; G08B 5/36; G08B 6/00; A61B 5/103; A61B 5/16; A61B 5/6801; A61B 2562/0219
See application file for complete search history.

(56) References Cited

U.S. PATENT DOCUMENTS

| | | |
|---|---|---|
| 4,524,773 A | 6/1985 | Fischell et al. |
| 5,723,786 A | 3/1998 | Klapman |

(Continued)

OTHER PUBLICATIONS

Hykso.com website (C) 2016.
Mashable.com website Jul. 3, 2014.
Striketec.com.website (C) 2016.

*Primary Examiner* — Joseph H Feild
*Assistant Examiner* — Rufus C Point
(74) *Attorney, Agent, or Firm* — Preti Flaherty Beliveau & Pachios LLP

(57) ABSTRACT

A method for behavior monitoring using a wearable detector is described. The method includes detecting a force of a patient action using the detector worn by the patient. The patient action is characterized as a behavior based on a location of the detector; and a frequency of the force, a magnitude of the force, a direction of the force and/or one or more threshold values. A determination is made as to whether to transmit a notification based at least in part on the behavior characterized. In response to a determination to transmit a notification, the notification is transmitted. Apparatus and computer readable media are also described.

17 Claims, 4 Drawing Sheets

(51) Int. Cl.
*G08B 3/10* (2006.01)
*G08B 6/00* (2006.01)
*G08B 5/36* (2006.01)

(56) References Cited

U.S. PATENT DOCUMENTS

| | | | |
|---|---|---|---|
| 7,981,058 B2 | 7/2011 | Akay | |
| 8,075,499 B2* | 12/2011 | Nathan | A61B 5/1107 |
| | | | 600/587 |
| 2007/0136102 A1* | 6/2007 | Rodgers | A61B 5/1113 |
| | | | 705/3 |
| 2008/0001735 A1* | 1/2008 | Tran | G06F 19/3418 |
| | | | 340/539.22 |
| 2008/0222769 A1* | 9/2008 | Natonson | A61H 9/0078 |
| | | | 2/70 |
| 2009/0062696 A1* | 3/2009 | Nathan | A61B 5/1107 |
| | | | 600/595 |
| 2009/0069642 A1* | 3/2009 | Gao | A61B 5/02055 |
| | | | 600/300 |
| 2010/0029770 A1* | 2/2010 | Roberts | A61K 31/195 |
| | | | 514/567 |
| 2013/0141233 A1* | 6/2013 | Jacobs | G08B 19/00 |
| | | | 340/521 |
| 2014/0159903 A1 | 6/2014 | Tropper et al. | |
| 2014/0163428 A1 | 6/2014 | Tropper et al. | |
| 2014/0197963 A1 | 7/2014 | Park et al. | |
| 2014/0303523 A1 | 10/2014 | Hong et al. | |
| 2014/0375461 A1* | 12/2014 | Richardson | G08B 21/0446 |
| | | | 340/573.7 |
| 2015/0068069 A1* | 3/2015 | Tran | H04B 1/385 |
| | | | 36/136 |
| 2015/0254956 A1* | 9/2015 | Shen | G08B 21/0446 |
| | | | 340/573.1 |
| 2016/0256080 A1* | 9/2016 | Shen | A61B 5/1115 |
| 2016/0287939 A1 | 10/2016 | Deochand et al. | |
| 2018/0075293 A1* | 3/2018 | Schinas | G06K 9/00335 |

* cited by examiner

TARGET BEHAVIOR MONITORING SYSTEM

This patent application claims priority from U.S. Provisional Patent Application No.: 62/414,163, filed Oct. 28, 2016, the disclosure of which is incorporated by reference herein in its entirety.

STATEMENT REGARDING FEDERALLY SPONSORED RESEARCH OR DEVELOPMENT

N/A

BACKGROUND OF THE INVENTION

Various embodiments relate generally to behavior monitoring systems, methods, devices and computer programs and, more specifically, relate to recording the behaviors of a human in order to track, analyze, and prevent current and future problem behaviors.

This section is intended to provide a background or context. The description may include concepts that may be pursued, but have not necessarily been previously conceived or pursued. Unless indicated otherwise, what is described in this section is not deemed prior art to the description and claims and is not admitted to be prior art by inclusion in this section.

The current state of the art is a manual method, where the behavior therapist will manually record occurrences of behavior by marking on a sheet of paper, or by manually inputting data into an electronic device such as a tablet of portable phone (and other ways), and/or give qualitative descriptions of the level of force used in a particular behavior. Both the manual nature of the data collection, as well as the subjective measurement are very prone to error, particularly, the force "measurement" or estimation.

Secondly, there is no method currently available that will automatically alert the appropriate person(s) to intervene when a problem behavior is occurring. This can be extremely dangerous to the individual if it goes undetected.

Lastly, with respect to the delivery of a notification, what is needed is a device that remedies the existing need for an active observer in the field.

BRIEF SUMMARY OF THE INVENTION

The below summary is merely representative and non-limiting.

The above problems are overcome, and other advantages may be realized, by the use of the embodiments.

In a first aspect, an embodiment provides a method for behavior monitoring. The method includes detecting a force of a patient action using detector worn by the patient (e.g., the person who's actions are being monitored). The patient action is characterized as a behavior based on a location of the detector; and a frequency of the force, a magnitude of the force, a direction of the force and/or one or more threshold values. A determination is made as to whether to transmit a notification based at least in part on the behavior characterized. In response to a determination to transmit a notification, the notification is transmitted (e.g., to a user operating a behavior monitoring system for the patient).

BRIEF DESCRIPTION OF THE SEVERAL VIEWS OF THE DRAWINGS

Aspects of the described embodiments are more evident in the following description, when read in conjunction with the attached Figures.

DETAILED DESCRIPTION OF THE INVENTION

Target behaviors may materialize as acute aggressive behavior directed toward one-self (self-injurious behavior), others (aggression to others), or items in the environment (aggression to the environment or environmental/property destruction). In various embodiments, target behavior is defined as any acute behavior emitted by the patient with the intent to cause damage to the patient's own body, to another person, or to something/property in the environment. These target behaviors can be further characterized as behaviors for which the monitoring, assessment, and/or treatment thereof has (or has the potential to have) direct habilitative and/or rehabilitative value to the patient, such as in conjunction with some systematic and evidence-based approach to intervention such as behavioral, pharmacological, psychiatric, psychological, or other form(s) of evidence-based therapeutic interventions with professionals appropriately qualified to treat such behavior.

Figure 1:
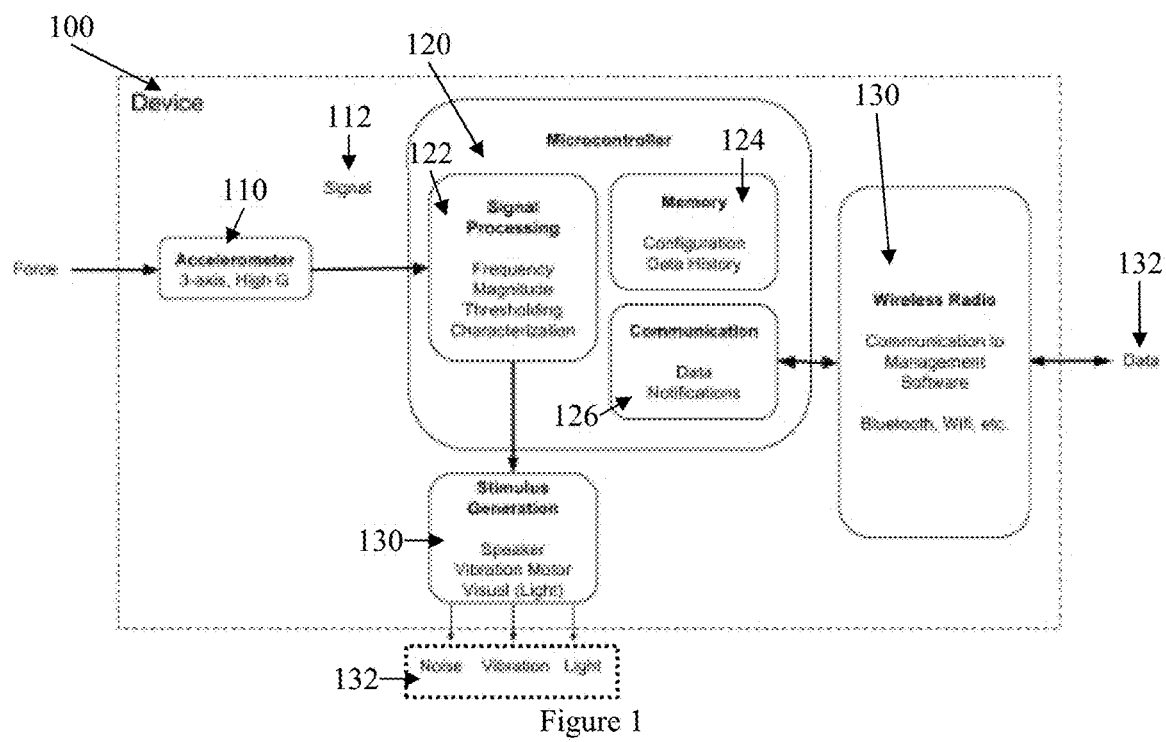
FIG. 1 shows a simplified block diagram of a device that is suitable for practicing various embodiments.

FIG. 1 shows a simplified block diagram of a device 100 that is suitable for practicing various embodiments. The device includes an accelerometer 110 which measures a force from a patient's motions and produces a signal 112 that is sent to the microcontroller 120. The signal is processed by a signal processor 122, based at least in part on configuration and data history stored in memory 124 in order to characterize the motions. Due to the characterization of the motion, the microcontroller may cause the device to provide a notice 132 to the patient, such as noise, vibration, light, etc. using a stimulus generator 130 and/or may send data 132 to notify a patient supervisor or caregiver, for example, via a wireless radio 130. The data 132 may be prepared using a communication sub-component 126 of the microcontroller 120.

As used in the non-limiting embodiment shown in FIG. 1:

Force—Motion created by self-injurious behavior. Acute acceleration in a 3-dimensional space.

Accelerometer (3-axis, High G) 110—Integrated circuit capable of measuring the acceleration of the device.

Signal 130—Analog or digital signal that other components of the device 100 are capable of interpreting.

Microcontroller 120—Integrated circuit containing a microprocessor, memory 124, and inputs and outputs monitor and control components of the device. Also known as a System on a Chip.

Signal Processing Component 122—Firmware code for the microcontroller 120 that interprets the signals 122 from the measurement devices. The signals are filtered and processed to indicate Frequency, Magnitude, Thresholding, and Characterization of the self-injurious behavior of the patient.

Notice Generation 132—Speaker, Vibration Motor and/or visual (e.g., Light, LED) for signaling to the patient that a certain self-injurious behavior has occurred.

Memory 124—Onboard RAM and Flash memory for maintaining device configuration and signal processing data.

Device Configuration—Connection settings, Thresholding settings, Notice settings, Calibration Data, Temporary Data, etc.

Communication (Wireless Radio) 130—Technology such as Bluetooth or Wifi for data communication between device 100 and Management Software running on a third party device.

Management Software—Custom software that runs on a wireless enabled device (PC, Tablet, Smartphone, etc.) that is capable of logging data, configuring the device 100, and actively notifying the observer of events.

Steps Describing How to Use

In one non-limiting embodiment, a behavior monitoring device may be used as follows:
1. User (non-patient) Launches Configuration Management software
2. User (non-patient) identifies which appendage the device(s) are attached to
3. User (non-patient) sets the force limit(s) for the individual that trigger events
   a. Events are behaviors that are then recorded and processed
   b. If there is more than 1 threshold, zones can be configured
      i. Zones are defined by upper and lower force thresholds
4. Users (non-patients) are able to configure notification settings based upon any combination of the following parameters, per each location the device is secured to on the body (e.g. left hand, right hand, head, leg, torso, etc.):
   a. Rate
      i. The number of events during a recorded session presented relative to a selected unit of time. E.g., Events per 1 minute, 10 minutes, 1 hour, 1 day
   b. Magnitude
      i. The force exerted during an event that exceeds a pre-determined threshold. E.g., a low event (200-400 RFU's), a medium event (400-600 RFU's), a high event (600-800 RFU's), and/or any other delineation levels created by the user
   c. Behavior type categorization
      i. When an event occurs by exceeding the pre-determined threshold, the behavior will be categorized in terms of a Slap, Punch, Slam, or any other directionality typing. The categorization may also be based on the directionality of the force.
   d. Examples of notification settings using the above parameters:
      i. 10 events occurring above the set threshold in a 10 minute period with the left hand
      ii. 10 events occurring above the set threshold in a 10 minute period with the left and right hand
      iii. 10 events occurring above the set threshold in a 10 minute period, with a high event setting (600-800 RFU's) with only the right hand
      iv. 10 events occurring above the set threshold in a 10 minute period, with a high event setting (600-800 RFU's) with the left and right hand, only occurring in a punch categorization.
      1) These are just examples, but any and all combinations of the above parameters can be configured to generate a notification.
5. Users (non-patients) are able to configure the notice settings based upon section 4 above.
   a. Notice options include but are not limited to:
      i. Vibration (weighted motor, piezo vibrator, etc.)
      ii. Sound (tones, music clips, etc.)
      iii. Visual (Light Emitting Diodes)
6. Users (non-patients) periodically connect (wirelessly) to the device to sync the data and store it
   a. PC/Tablet/Smartphone
7. The device can report all data based upon the configuration data sent above
   a. Users (non-patients) can connect and change the settings when desired
8. Periodic battery charging
   a. The device can notify the user (non-patient) as to when this is recommended The Target Behavior Monitoring System functions may be as follows:
1) Automatically record the frequency and magnitude of behaviors
   a. These behavior thresholds (force levels) are configurable based upon the magnitude of the behaviors under analysis
   b. All measurements are time stamped with the magnitude
   c. Behavior type categorization (Slap, punch, pound, etc.)
   d. All combinations of magnitude, frequency & behavior type categorization
      i. E.g.: Magnitude, and frequency of a certain behavior type categorization
2) Notifications to the appropriate person(s) who are responsible for the individual when a behavior is occurring
   a. Notifications can be configured based upon any of the above mentioned criteria
      i. Magnitude, Frequency and behavior type categorization
   b. Notifications can be via provided by any suitable wireless technology, such as, WiFi or SMS to another device
3) Based upon the above functions, the option to deliver a notice to the individual based upon pre-set criteria is available.

The Target Behavior Monitoring System may be a wearable, small form factor device that can be worn on an appendage or appendages, similar to a small watch, wristband, headband, or helmet. The Target Behavior Monitoring System is tightly attached to the body, so that there is minimal to no movement outside of the natural movement of the arm (or other appendages). The attachment to the body must be comfortable and non-distracting, so that individuals do not alter their behavior because of it. One embodiment of this would be in a fabric wristband, or a form-fitting/snug rubber bracelet. The Target Behavior Monitoring System may include multiple wearable detects which communicate with each other and/or with a processing device (which may itself incorporate a detector). This communication may be via a wired connection and/or via a wireless connection.

After the device is attached to the individual, a calibration is performed in order to determine the force at which a target behavior occurs. This calibration of force can be used to distinguish behaviors monitored and reported by this device. The therapists determines how to establish the threshold based upon their treatments, but the therapist can then set the amount of the force thresholds (upper and lower bounds). This threshold is then stored on the device.

Accelerometers may be used to measure the acceleration of the forces exhibited by the target behaviors. When the calibrated force level is exceeded, the value is stored on the device with the appropriate timestamp. In one non-limiting embodiment forces above the calibrated limit are recorded. The data can then be reviewed by downloading the data to a computer or a mobile device.

The device monitors behaviors of an individual (as described above) and alerts the appropriate person(s) when a problem behavior is occurring so they can intervene. These notifications can be sent to another device such as a computer network or a mobile smartphone.

In addition, this Target Behavior Monitoring System also includes a distinct notice (auditory, visual, tactile, etc.) that can be emitted based on the behavior or based on a given criteria of a behavioral event or events. Criteria for a behavior are programmed for each individual. These criteria will be able to be set by the therapist, which include the frequency, magnitude and the topographical orientation.

Figure 2:
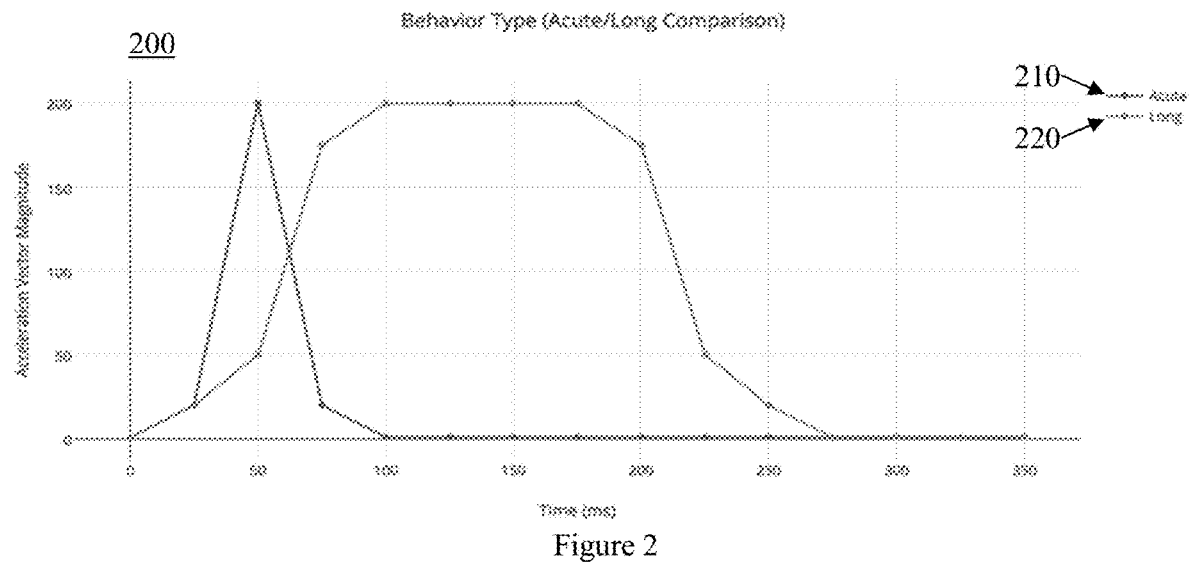
FIG. 2 is a graph showing example settings for acute/long classification of detected behaviors.
Figure 3:
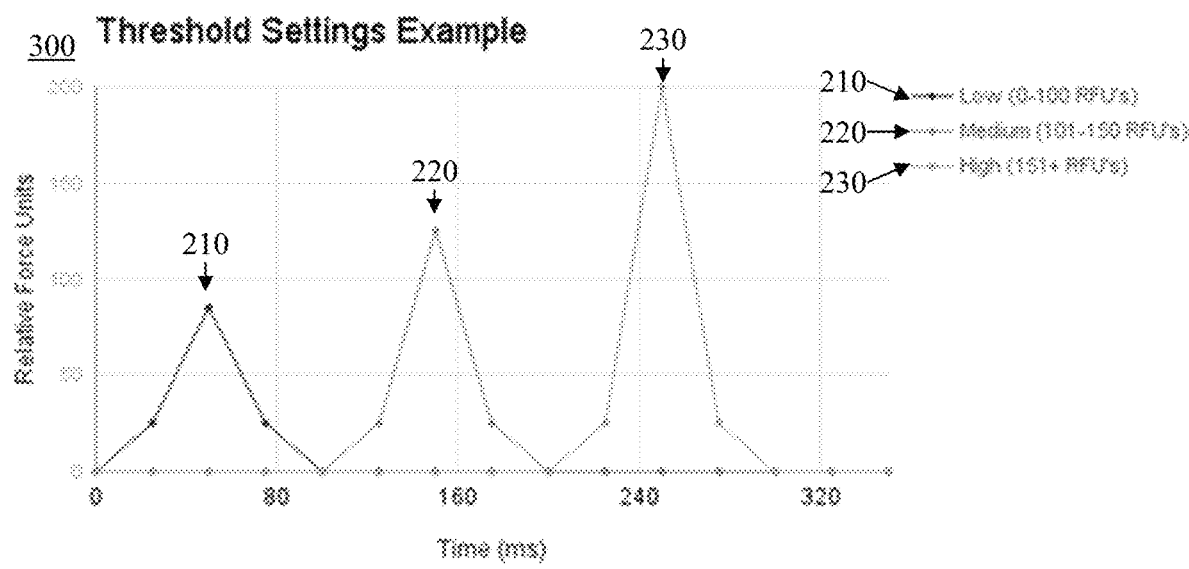
FIG. 3 is a graph showing example settings for threshold classification of detected behaviors.
Figure 4:
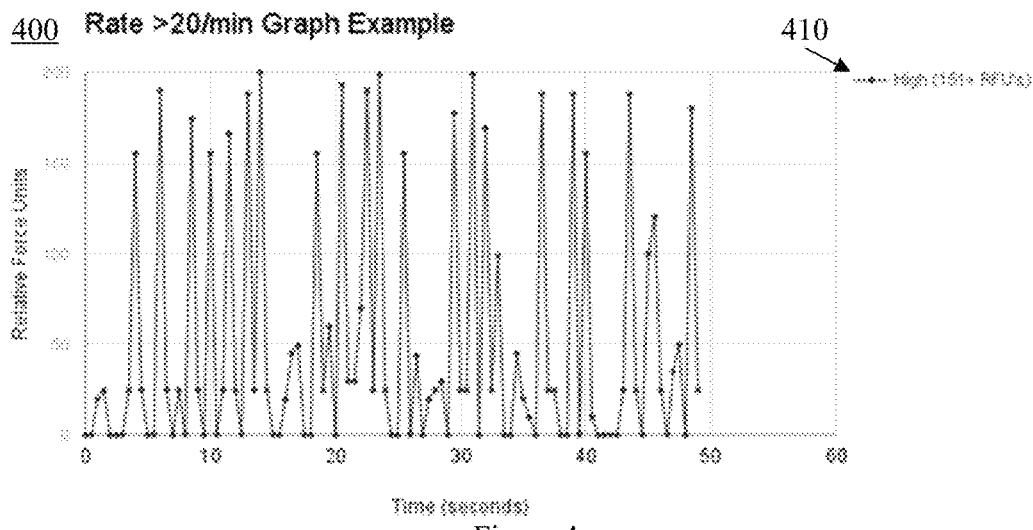
FIG. 4 is a graph showing an example of detected force over a length of time.

A non-limiting use case is as follows:

1. User (non-patient) launches the software to configure the device
2. User (non-patient) identifies the device as being attached to the arm (other options include: Head/Leg/Waist/etc.)
   a. Each sensor may be identified independently, so that multiple sensors on the client can be monitored at the same time.
      i. e.g., If the client tends to aggress with their arms and their legs, then monitoring 4 sensors can give full coverage.
   b. Each option (Arm/Leg/Head) may have slightly different filtering for non-acute events (see 3) c.iii. below)
      i. Alternatively, they can have similar or identical filtering equations.
3. User (non-patient) identifies 3 ranges of force for analysis
   a. Low Range (e.g., 0-100 RFUs)
   b. Medium Range (e.g., 101-150 RFUs)
   c. High Range (e.g., 151+RFUs)
      i. RFUs are "Relative Force Units". The force measurements are relative to the mass of the individual's arm (or leg/head).
      ii. Relative force units are calculated by the device using the Acceleration Vector Magnitude equation: $\sqrt{X^2+Y^2+Z^2}$
      iii. Filtering is used to identify acute self-injurious events from normal behavior events
         1. Even with the ability to trigger a notification based on thresholding limit(s) introduced by the user, the device prevents "Long" events such as arm swinging, walking, normal behavior, etc. from affecting the frequency of the self-injurious behaviors. This filtering is performed on the device and does not prevent an "Acute" event notifications such as when the device abruptly stops upon contact with another object. A visualization of Acute vs. Long is show in FIG. 2.
         2. FIG. 2 is a graph 200 showing example settings for acute 210/long 220 classification of detected behaviors. The Y axis in the plot is the vector magnitude of the acceleration of the device. This value is created using the X, Y, Z axis components of the acceleration reported by the accelerometer. As mentioned above, the Acceleration Vector Magnitude=$\sqrt{X^2+Y^2+Z^2}$
         3. The high magnitude acceleration over a long period, over 0.5 seconds, would indicate a swinging event that should be filtered out. The long period of high magnitude acceleration does not represent an acute event or impact.
      iv. FIG. 3 is a graph 300 showing example settings for threshold classification of detected behaviors. Users (non-patients) can set multiple ranges, this is a non-limiting example of one setting. As shown, the ranges include low 210, medium 220, and high 230 thresholds. In other embodiments, more or less thresholds may be used. These thresholds may be strictly greater than or less than thresholds or they include the threshold value (e.g., a greater than or equal to threshold)
4. Users (non-patients) selects the notifications to occur when given conditions apply, for example:
   a. Events are in the High Range (notifications can be set for one defined range)
   b. The rate of High Range Events is ≥20/min. FIG. 4 is a graph 400 showing an example of detected force 410 over a length of time.
   c. The aggression type is a punch (see Acceleration direction below).
      i. Acceleration direction filtering is based upon which axis and whether it was positive or negative that the majority of the acceleration is occurring. A punching motion that results in contact with a solid object would register the highest in the positive y direction and would indicate a 'punching' type of aggression. However, the operator may want to filter out events that register as highest in the positive X direction as that may indicate a less aggressive behavior, such as slamming a first on a table.
      ii. Similar actions may be filtered into a single category. For example a first Slam and a Chopping action could be done both on a table or against a wall and would fall under the same type categorization.
      iii. Below are some example behavior type categorizations that are predefined for the arm, head and leg sensors. The operator would be able to create their own based on which magnitudes they expect to be the highest in the positive or negative direction for a particular behavior they are filtering for or against.

Table 1 illustrates one non-limiting example of the distinction between various Type categorization, such as between a punch and a hit.

TABLE 1

| Type categorization | Sensor Location | X (magnitude) | Y (magnitude) | Z (magnitude) |
|---|---|---|---|---|
| Punch | Arm (Wrist) | Low | High (positive) | Low |
| Hit with Elbow | Arm (Wrist) | Low | High (negative) | Low |
| Slap/Open Hand Slam | Arm (Wrist) | Low | Low | High (negative) |
| Fist Slam/Chop | Arm (Wrist) | High (positive) | Low | Low |
| Forehead Impact | Head (Helmet) | Low | High (positive) | Low |
| Back of Head Impact | Head (Helmet) | Low | High (negative) | Low |
| Kick | Leg (Ankle) | High (or Z) | Low | High (or X) |
| Stomp | Leg (Ankle) | Low | High | Low |
| Arm to Head | Arm and Head | Any High (see below) | | | iv. The notifications occur when the user's application is running (and connected)

v. During post processing or while the user's application is running an additional characterization of arm to head contact can be identified when acute events happen on multiple sensors at the same time. Since acute events could happen on both sensors when they are not coming in contact with each other, the user can decide whether the fact that the events happed simultaneously is useful information for determining a particular behavior.

vi. Notifications can be provided for a guardian's use as well

5. The user (non-patient) sets the vibrating notice to occur when an event occurs in the Medium range.
   a. The user (non-patient) can set when the notice is applied, similar to how the thresholds were set above.

6. Sync options can be set to sync anytime the App is opened and/or at regular intervals (e.g., after 6 hours)
   a. Syncing (data transfer to another device (e.g., a smartphone or a tablet)) can occur when the operator has the application running As described above, various embodiments provide a method, apparatus and computer program(s) to track, analyze, and prevent current and future problem behaviors based on recorded behaviors.

Figure 5:
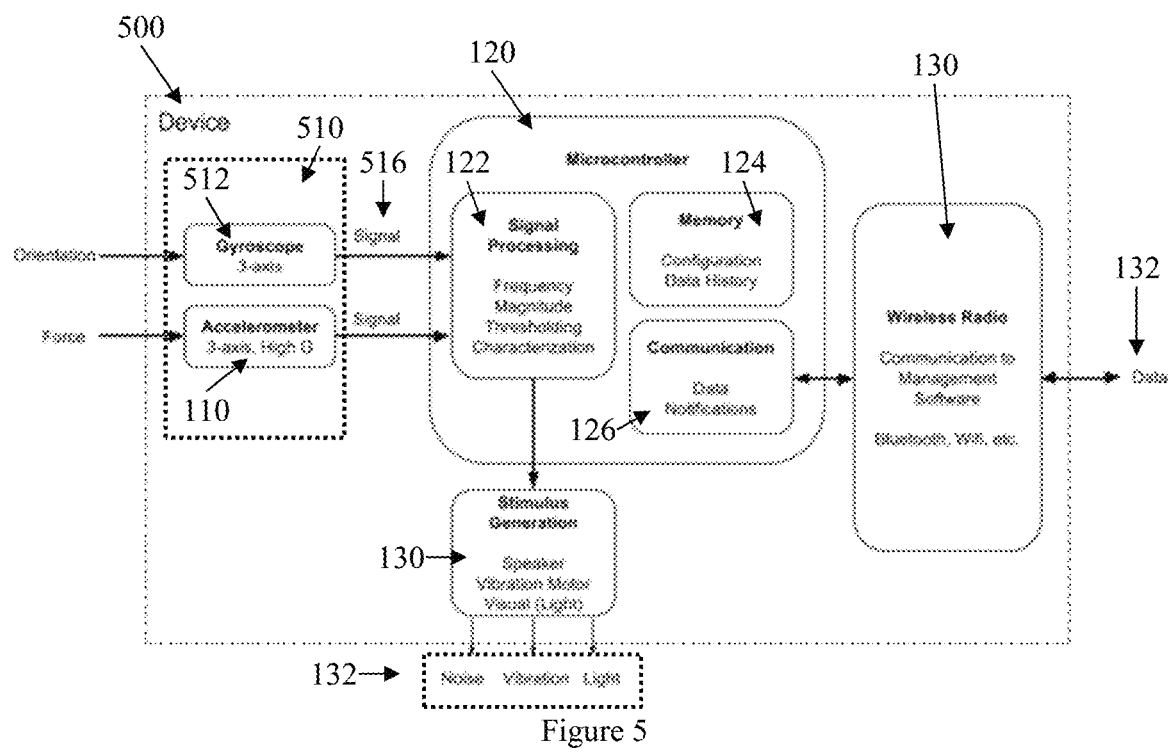
FIG. 5 shows a simplified block diagram of an alternative device that is suitable for practicing various embodiments.

FIG. 5 shows a simplified block diagram of an alternative device 500 that is suitable for practicing various embodiments. This device is similar to the one shown above in FIG. 1. In this non-limiting embodiment, a detector 510 is used. The detector includes the accelerometer 110 and a gyroscope 512 which may be used to detection device/limb orientation. Orientation includes the pitch (rotation about Y axis), roll (rotation about X axis), and yaw (rotation about Z axis) of device attached to patient. The detector 510 provides signal 516 based on the accelerometer 110 and a gyroscope 512 to the microcontroller 120.

In addition, criteria for a behavior may include the topographical orientation of the device during the action and/or any change in orientation during the action.

Orientation filtering uses the gyroscope 512 which allows for filtering based on the orientation of the device upon maximum force or the change in orientation during motion between surpassing the threshold and maximum force. Events could be further filtered by orientation filtering by indicating whether a first is slamming against a horizontal surface (floor, table, patient's leg when sitting) or a vertical surface (non-patient, wall, sides of furniture). The following table lists the orientations which, in this non-limiting example, use a range of +/−30 degrees for reliable detection.

Table 2 illustrates one non-limiting example of various event categorizations using type categorizations and detector data.

TABLE 2

| Orientation of Arm | Type from Table 1 | Pitch (degrees) | Roll (degrees) | Yaw (degrees) |
|---|---|---|---|---|
| Event on horizontal surface | Punch | −90 | Any | 0 |
| Event on vertical surface | Punch | 0 | 0 to 90 | Any |
| Event on horizontal surface | Slap/Open Hand Slam | 0 | 0 | Any |
| Event on vertical surface | Slap/Open Hand Slam | 90 | Any | 0 |
| Event on horizontal surface | Fist Slam/Chop | Any | 90 | 0 |
| Event on vertical surface | Fist Slam/Chop | 90 | Any | 90 |
| Orientation Unchanged (straight motion) | Any | Change <30 degrees from surpassing threshold to maximum force | | |
| Orientation Changed (hooking/arcing motion) | Any | Change >30 degrees from surpassing threshold to maximum force | | |

In a further, non-limiting embodiment, self-injurious behaviors may be distinguished from the types of target behavior based on the movement, for example, based upon which axes the movement is along (e.g., "forward punch", "upward punch", slap, etc.). The end user (such as the care giver) can create their own labels for the different activities/ responses that are to be measured as they go through a calibrating process.

As described above, various embodiments provide a method, apparatus and computer program(s) to record, track and analyze the behaviors of a human, in order to prevent current and future problem behaviors.

Figure 6:
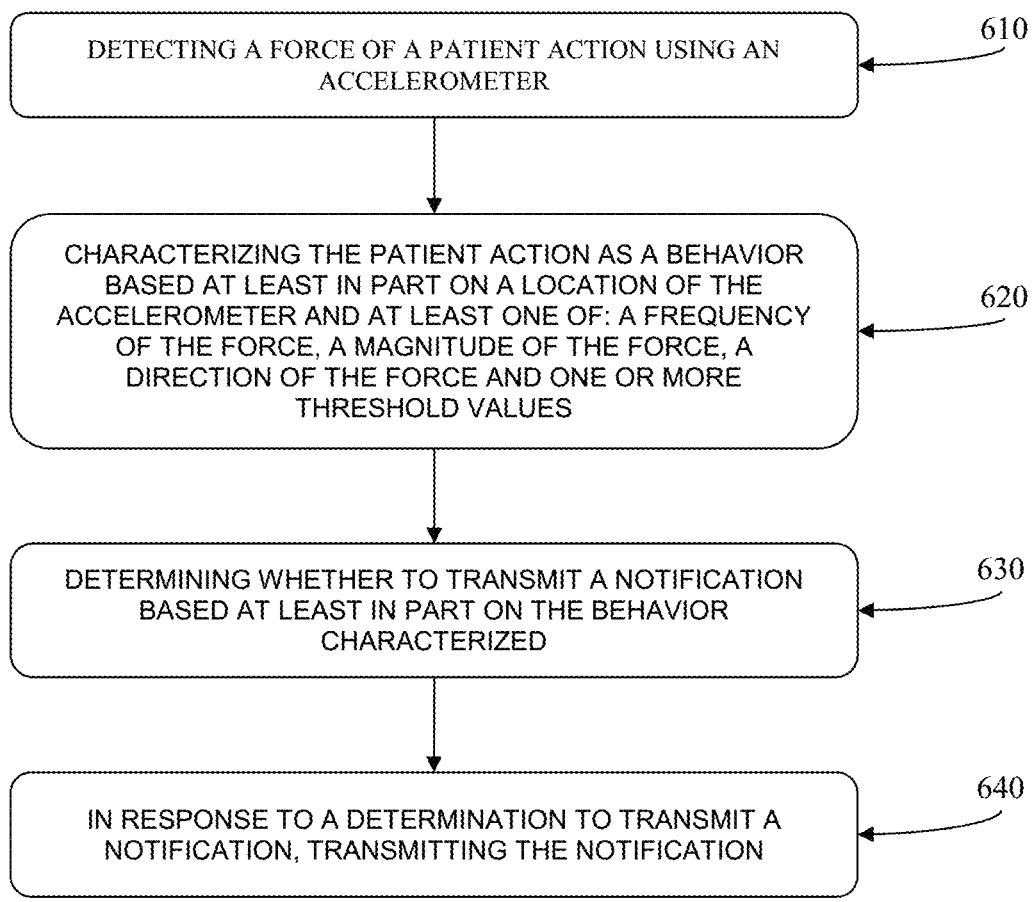
FIG. 6 is a logic flow diagram illustrating a method, and a result of execution of computer program instructions embodied on a memory, in accordance with an embodiment.

FIG. 6 is a logic flow diagram that illustrates a method, and a result of execution of computer program instructions, in accordance with various embodiments. In accordance with an embodiment a method performs, at Block 610, a step of detecting a force of a patient action using an accelerometer. At Block 620, the method performs a step of characterizing the patient action as a behavior based at least in part on a location of the accelerometer and a frequency of the force, a magnitude of the force, a direction of the force and/or one or more threshold values. A determination is made as to whether to transmit a notification based at least in part on the behavior characterized at Block 630. At Block 620, in response to a determination to transmit a notification the method performs a step of transmitting the notification.

The various blocks shown in FIG. 6 may be viewed as method steps, as operations that result from use of computer program code, and/or as one or more logic circuit elements constructed to carry out the associated function(s).

An embodiment provides a method for behavior monitoring. The method includes detecting a force of a patient action using detector worn by the patient. The patient action is characterized as a behavior based at least in part on (a) a location of the detector and (b) a frequency of the force, a magnitude of the force, a direction of the force and/or one or more threshold values. A determination is made as to whether to transmit a notification based at least in part on the behavior characterized. In response to a determination to transmit a notification, the notification is transmitted.

In another embodiment of the method above, the method also includes determining whether to notify the patient based at least in part on the behavior characterized; and in response to a determination to transmit a notification, generating a notice. The notice can be a noise, a vibration and/or a light.

In a further embodiment of any one of the methods above, the method also includes receiving a configuration specifying at least one of: the location of the detector and the one or more threshold values.

In another embodiment of any one of the methods above, detecting the force also includes detecting an orientation of gyroscope located on the patient. Characterizing the patient action is also based on the orientation of the gyroscope.

In a further embodiment of any one of the methods above, characterizing the patient action as a behavior includes determining whether the patient action is a self-injurious behavior. The patient action can be determined to be a self-injurious behavior in response to the force of the patient action being directed at the patient. Detecting a force of a patient action using a detector may include detecting the force of the patient action using a first detector. The method may also include detecting an impact received by the patient using a second detector. The patient action can then be determined to be a self-injurious behavior in response to the patient action occurring approximately simultaneously with the impact received by the patient. Determining whether to transmit a notification can include making a determination to transmit a notification when the patient action is characterized as a self-injurious behavior.

In another embodiment of any one of the methods above, the detector includes a gyroscope and/or an accelerometer.

In a further embodiment of any one of the methods above, characterizing the patient action as a behavior is based at least in part on a location of the accelerometer detector and a frequency of the force. The patient action is determined to be a repetitive behavior when the patient action repeats a number of times within a time period greater than or equal to a threshold frequency. Determining whether to transmit a notification includes determining to transmit a notification in response to the patient action being characterized as a repetitive behavior.

Another embodiment provides an apparatus for behavior monitoring. The apparatus includes a detector configured to be worn by a patient and to detect a force of a patient action. The apparatus also includes at least one processor; and at least one memory including computer program code. The at least one memory and the computer program code are configured to, with the at least one processor, cause the apparatus to characterize as a behavior based at least in part on (a) a location of the detector and (b) a frequency of the force, a magnitude of the force, a direction of the force and/or one or more threshold values; determine whether to transmit a notification based at least in part on the behavior characterized; and in response to a determination to transmit a notification, transmit the notification.

In a further embodiment of any one of the apparatus above, the apparatus is embodied in an integrated circuit.

In another embodiment of the apparatus above, the apparatus is embodied in a wearable device.

A further embodiment provides a computer readable medium for behavior monitoring. The computer readable medium is tangibly encoded with a computer program executable by a processor to perform any one of the methods described above.

In another embodiment of the computer readable medium above, the computer readable medium is a non-transitory computer readable medium (e.g., CD-ROM, RAM, flash memory, etc.).

In a further embodiment of any one of the computer readable media above, the computer readable medium is a storage medium.

Various operations described are purely exemplary and imply no particular order. Further, the operations can be used in any sequence when appropriate and can be partially used. With the above embodiments in mind, it should be understood that additional embodiments can employ various computer-implemented operations involving data transferred or stored in computer systems. These operations are those requiring physical manipulation of physical quantities. Usually, though not necessarily, these quantities take the form of electrical, magnetic, or optical signals capable of being stored, transferred, combined, compared, and otherwise manipulated.

Any of the operations described that form part of the presently disclosed embodiments may be useful machine operations. Various embodiments also relate to a device or an apparatus for performing these operations. The apparatus can be specially constructed for the required purpose, or the apparatus can include a general-purpose computer selectively activated or configured by a computer program stored in the computer. In particular, various general-purpose machines employing one or more processors coupled to one or more computer readable medium, described below, can be used with computer programs written in accordance with the teachings herein, or it may be more convenient to construct a more specialized apparatus to perform the required operations.

The procedures, processes, and/or modules described herein may be implemented in hardware, software, embodied as a computer-readable medium having program instructions, firmware, or a combination thereof. For example, the functions described herein may be performed by a processor executing program instructions out of a memory or other storage device.

The foregoing description has been directed to particular embodiments. However, other variations and modifications may be made to the described embodiments, with the attainment of some or all of their advantages. Modifications to the above-described systems and methods may be made without departing from the concepts disclosed herein. Accordingly, the invention should not be viewed as limited by the disclosed embodiments. Furthermore, various features of the described embodiments may be used without the corresponding use of other features. Thus, this description should be read as merely illustrative of various principles, and not in limitation of the invention.

What is claimed is:

1. A method for behavior monitoring, the method comprising: for each occurrence of a patient action event in a plurality of patient action events by a patient:
   detecting a force of each individual action in the patient action event using a detector worn by the patient; and characterizing, by a processing device, the patient action event as a behavior from a plurality of potential behaviors based at least in part on a location of the detector and, for each individual action in the patient action event, at least one of: a magnitude of the force of the individual action, a direction of the force of the individual action and one or more threshold values, wherein characterizing the patient action event includes determining whether the patient action event is a self-injurious behavior by determining that the patient action event includes an acute aggressive action by the patient which is directed toward the patient, wherein characterizing the patient action event as a behavior is further based at on a frequency of the force;

automatically determining, by the processing device, whether to transmit a notification based at least in part on a frequency of patient action events from the plurality of patient action events which are characterized as the same type of behavior, wherein the patient action event is determined to be a repetitive behavior when the patient action repeats a number of times within a time period greater than or equal to a threshold frequency, and wherein determining whether to transmit a notification includes determining to transmit a notification in response to the patient action event being characterized as a repetitive behavior; and in response to a determination to transmit a notification, transmitting the notification.

2. The method of claim 1, further comprising:
determining whether to notify the patient based at least in part on the behavior characterized; and
in response to a determination to transmit a notification, generating a notice,
wherein the notice is at least one of: a noise, a vibration and a light.

3. The method of claim 1, further comprising receiving a configuration specifying at least one of the location of the detector and the one or more threshold values.

4. The method of claim 1, wherein detecting the force further comprises detecting an orientation of a gyroscope located on the patient, and
wherein characterizing the patient action event is further based on the orientation of the gyroscope.

5. The method of claim 1 wherein the patient action event is determined to be a self-injurious behavior in response to the force of the patient action event being directed at the patient.

6. The method of claim 1 wherein detecting a force of a patient action event using a detector includes detecting the force of the patient action event using a first detector;
wherein the method further comprises detecting an impact received by the patient using a second detector; and
wherein the patient action event is determined to be a self-injurious behavior in response to the patient action event occurring simultaneously with the impact received by the patient.

7. The method of claim 1 wherein determining whether to transmit a notification includes making a determination to transmit a notification when the patient action event is characterized as a self-injurious behavior.

8. The method of claim 1, wherein the detector includes at least one of: a gyroscope and an accelerometer.

9. An apparatus, comprising at least one processor; and at least one memory including computer program code, the at least one memory and the computer program code configured to, with the at least one processor, cause the apparatus to perform at least the following:

for each occurrence of a patient action event in a plurality of patient action events by a patient:
detect a force of each individual action in the patient action event using a detector worn by the patient; and
characterize the patient action event as a behavior from a plurality of potential behaviors based at least in part on a location of the detector and, for each individual action in the patient action event, at least one of: a magnitude of the force of the individual action, a direction of the force of the individual action and one or more threshold values, wherein characterizing the patient action event includes determining whether the patient action event is a self-injurious behavior by determining that the patient action event includes an acute aggressive action by the patient which is directed toward the patient, wherein characterizing the patient action event as a behavior is further based at on a frequency of the force;

automatically determine whether to transmit a notification based at least in part on a frequency of patient action events from the plurality of patient action events which are characterized as the same type of behavior, wherein the patient action event is determined to be a repetitive behavior when the patient action repeats a number of times within a time period greater than or equal to a threshold frequency, and wherein determining whether to transmit a notification includes determining to transmit a notification in response to the patient action event being characterized as a repetitive behavior; and in response to a determination to transmit a notification, transmit the notification.

10. The apparatus of claim 9, further comprising the detector worn by the patient.

11. The apparatus of claim 10, wherein the detector worn by the patient comprises a gyroscope configured to detect an orientation of the detector located on the patient,
wherein the at least one memory and the computer program code are further configured to cause the apparatus to further characterize the patient action event based on the orientation of the gyroscope.

12. The apparatus of claim 9, further comprising an output device,
wherein, the at least one memory and the computer program code are further configured to cause the apparatus to determine whether to notify the patient based at least in part on the behavior characterized; and
in response to a determination to generate a notice using the output device.

13. The apparatus of claim 12, wherein the output device is at least one of: a speaker, a vibration engine, and a light.

14. A non-transitory computer readable medium tangibly encoded with a computer program executable by a processor to perform actions comprising:
for each occurrence of a patient action event in a plurality of patient action events by a patient;
detecting a force of each individual action in the patient action event using a detector worn by the patient; and
characterizing the patient action as a behavior from a plurality of potential behaviors based at least in part on a location of the detector and, for each individual action in the patient action event, at least one of: a magnitude of the force of the individual action, a direction of the force of the individual action and one or more threshold values;

wherein characterizing the patient action event includes determining whether the patient action event is a self-injurious behavior by determining that the patient action event includes an acute aggressive action by the patient which is directed toward the patient, wherein characterizing the patient action event as a behavior is further based at on a frequency of the force;

automatically determining whether to transmit a notification based at least in part on a frequency of patient action events from the plurality of patient action events which are characterized as the same type of behavior, wherein the patient action event is determined to be a repetitive behavior when the patient action repeats a number of times within a time period greater than or equal to a threshold frequency, and wherein determining whether to transmit a notification includes determining to transmit a notification in response to the patient action event being characterized as a repetitive behavior: and in response to a determination to transmit a notification, transmitting the notification.

15. The computer readable medium of claim 14, wherein detecting the force further comprises detecting an orientation of a gyroscope located on the patient, and
wherein characterizing the patient action event is further based on the orientation of the gyroscope.

16. The computer readable medium of claim 14, wherein detecting a force of a patient action event using a detector includes detecting the force of the patient action event using a first detector;
wherein the method further comprises detecting an impact received by the patient using a second detector; and
wherein the patient action event is determined to be a self-injurious behavior in response to the patient action event occurring substantially simultaneously with the impact received by the patient.

17. A method for behavior monitoring of a patient, the method comprising:
detecting, a force of each individual action in a patient action event using a detector worn by the patient;
characterizing, by a processing device, the patient action event as a behavior from a plurality of potential behaviors based at least in part on a location of the detector and, for each individual action in the patient action event, at least one of: a magnitude of the force of the individual action, a direction of the force of the individual action and one or more threshold values,
wherein characterizing the patient action event includes determining whether the patient action event is a self-injurious behavior by determining that the patient action event includes an acute aggressive action by the patient which is directed toward the patient,
wherein characterizing the patient action event as a behavior is further based at on a frequency of the force;
automatically determining, by the processing device, whether to transmit a notification based at least in part on an analysis of the patient action event and at least one prior patient action event which occurred in a predetermined timeframe, wherein the patient action event and each of the at least one prior patient action event are characterized as the same type of behavior,
wherein the patient action event is determined to be a repetitive behavior when the patient action repeats a number of times within a time period greater than or equal to a threshold frequency, and
wherein determining whether to transmit a notification includes determining to transmit a notification in response to the patient action event being characterized as a repetitive behavior: and
in response to a determination to transmit a notification, transmitting the notification.

* * * * *